United States Patent [19]

McAtee et al.

[11] Patent Number: 5,607,980
[45] Date of Patent: Mar. 4, 1997

[54] TOPICAL COMPOSITIONS HAVING IMPROVED SKIN FEEL

[75] Inventors: David M. McAtee, Fairfield; Lourdes D. Albacarys, West Chester; Erik J. Hasenoehrl, Cincinnati; Joseph A. Listro, Loveland, all of Ohio

[73] Assignee: The Procter & Gamble Company, Cincinnati, Ohio

[21] Appl. No.: 505,988

[22] Filed: Jul. 24, 1995

[51] Int. Cl.$^6$ ............................................. A01N 47/10
[52] U.S. Cl. .................. 514/476; 252/153; 252/354; 252/355; 252/357; 252/555; 424/78.02; 424/78.03; 514/844; 510/130
[58] Field of Search ................. 514/476, 844, 514/846; 424/78.02, 78.03; 252/153, 545, 546, 550, 551, 555, 355, 354, 357

[56] References Cited

U.S. PATENT DOCUMENTS

| | | | |
|---|---|---|---|
| 4,166,048 | 8/1979 | Nishimura et al. | 252/546 |
| 4,243,549 | 1/1981 | Messenger et al. | 252/355 |
| 4,246,131 | 1/1981 | Lohr | 252/153 |
| 4,321,256 | 5/1982 | Hasegawa et al. | 424/70 |
| 4,555,360 | 11/1985 | Bissett et al. | 252/541 |
| 4,772,424 | 9/1988 | Greeb | 252/546 |
| 5,246,629 | 9/1993 | Fukumoto et al. | 252/546 |
| 5,387,373 | 2/1995 | Naik | 252/546 |

FOREIGN PATENT DOCUMENTS

| | | | |
|---|---|---|---|
| 247832 | 12/1987 | European Pat. Off. | C11D 1/94 |
| 373851 | 6/1995 | European Pat. Off. | C11D 1/94 |
| 3011549 | 10/1981 | Germany | C11D 1/14 |
| 3837985 | 5/1990 | Germany | A61K 7/07 |
| 63-309594 | 6/1987 | Japan . | |
| 63-313711 | 12/1988 | Japan | A61K 7/06 |
| 1081900 | 3/1989 | Japan | C11D 1/62 |
| 1135898 | 5/1989 | Japan | C11D 1/62 |
| 5017342 | 1/1993 | Japan | A61K 7/50 |
| 5194985 | 8/1993 | Japan | C11D 1/94 |
| 6293620 | 10/1994 | Japan | A61K 7/075 |
| 7025726 | 1/1995 | Japan | A61K 7/02 |
| 8703735 | 5/1987 | Spain | A61K 7/07 |
| 1306969 | 2/1973 | United Kingdom | C11D 1/12 |

OTHER PUBLICATIONS

J. Garcia Dominguez et al. International Journal of Cosmetic Science 3, 57–68 (1981) "The inhibitory effect of some amphoteric surfactants on the irritation potential of alkyl-sulphates".

*Primary Examiner*—Terressa Mosley
*Attorney, Agent, or Firm*—Anthony D. Sabatelli

[57] ABSTRACT

The compositions of the present invention are useful for topical application to human skin. These compositions provide improved skin feel. These compositions can be in the form of leave-on products or products that are rinsed or wiped from the skin after use. These compositions are also useful for conditioning desquamating, and cleansing the skin and for relieving dry skin.

21 Claims, No Drawings

TOPICAL COMPOSITIONS HAVING IMPROVED SKIN FEEL

TECHNICAL FIELD

The compositions of the present invention are useful for topical application to human skin. These compositions provide improved skin feel. These compositions can be in the form of leave-on products or products that are rinsed or wiped from the skin after use. These compositions are also useful for conditioning the skin, for desquamating the skin, for cleansing and clarifying the skin, for reducing skin pore size, and also for relieving dry skin.

BACKGROUND OF THE INVENTION

The treatment of human skin with various agents has been undertaken for many years with the goal being to keep the skin clean and in a smooth and supple condition. Skin has the tendency to dry out when exposed to low humidity or to harsh detergent solutions for extended periods of time. From a physiological standpoint, dryness is a measure of the water content of the skin. Under normal conditions, the water content and vapor pressure of the skin are higher than those of the surrounding air, with consequent evaporation of water from the skin's surface. Skin becomes dry because of excessive loss of water from its surface, which results in loss of water from the stratum corneum. Low humidity speeds up this process, exacerbating the drying of skin. Also, continuous and prolonged contact with or immersion in soap or detergent solutions can contribute to dryness of the stratum corneum. The reason for this is that these solutions promote dissolution of the skin surface and lipids, and the dissolution of the hygroscopic water-soluble components of the skin.

Also, in normal skin, the stratum corneum is shed as individual cells or as small clusters of cells. Skin problems such as dry skin, psoriasis, ichthyosis, dandruff, acne, callus, photodamaged skin, aged skin, and sunburn can be described as disorders of keratinization in which the shedding of stratum corneum cells at the skin surface is altered relative to normal, young, healthy skin. Such alteration results in shedding of large clusters of cells leading to visible scaling of the skin, a build-up of keratinaceous material on the surface or in follicles or ducts, and a rough texture to the skin surface. These conditions can be improved by removal of the outermost keratinaceous material. In other words, by desquamation.

Additionally there is an ongoing need to effectively deliver a wide variety of active ingredients to the skin, either via direct application of such a composition, or in the case of a cleansing composition, via the cleansing process.

Therefore, there is a need for topical skin care compositions which give the skin a smooth and elegant skin feel, which are useful for treating dry skin, and which are useful for providing a desquamation benefit. There is also a need for providing cleansing products have these attributes. There is also a need for composition which are also useful for delivering a wide variety of active ingredients to the skin, either directly to the skin or during the cleansing process.

It has been found in the present invention that skin care compositions containing a combination of amphoteric surfactants, anionic surfactants, and cationic surfactants are useful for providing these skin care benefits.

It is therefore an object of the present invention to provide skin care compositions for topical application to the skin.

It is another object of the present invention to provide skin care compositions having improved skin conditioning properties, and which are also mild and nonirritating to the skin.

It is another object of the present invention to provide skin care compositions which improve skin dryness and which give the skin a smooth, soft, silky feel.

It is another object of the present invention to provide skin care compositions which are useful delivering a wide variety of active ingredients to the skin.

It is another object of the present invention to provide skin care compositions, which, when in the form of cleansing compositions, are useful for delivering a wide variety of active ingredients to the skin via the cleansing process.

It is another object of the present invention to provide methods for treating the skin.

It is another object of the present invention to provide methods for cleansing the skin, for clarifying the skin, for reducing skin dryness, for reducing pore size, and for delivering active ingredients to the skin.

It is another object of the present invention to make the skin feel soft and smooth.

These and other objects will become readily apparent from the detailed description which follows.

SUMMARY OF THE INVENTION

The present invention relates to topical personal care compositions comprising:

(a) from about 0.1% to about 20% by weight of an amphoteric surfactant having the following structure

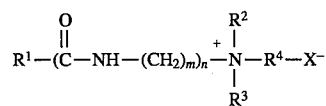

wherein $R^1$ is unsubstituted, saturated or unsaturated, straight or branched chain alkyl having from about 9 to about 22 carbon atoms; m is an integer from 1 to about 3; n is 0 or 1; $R^2$ and $R^3$ are independently selected from alkyl having from 1 to about 3 carbon atoms and monohydroxyalkyl having from about 1 to about 3 carbon atoms; $R^4$ is selected from saturated or unsaturated alkyl having from 1 to about 5 carbon atoms and saturated or unsaturated monohydroxyalkyl having from 1 to about 5 carbon atoms; X is selected from the group consisting of $CO_2$, $SO_3$, and $SO_4$; and pharmaceutically acceptable salts of the foregoing compounds;

(b) from about 0.1% to about 20% by weight of an anionic surfactant, (c) from about 0.1% to about 15% by weight of a cationic surfactant, and (d) from about 45% to about 99.7% by weight water.

The present invention also relates to methods for treating the skin, specifically to methods of conditioning, cleansing, clarifying, and desquamating the skin, for reducing pore size, and reducing skin dryness, utilizing these compositions.

The present invention also relates to methods of preparing compositions comprising:

(a) from about 0.1% to about 20% by weight of an amphoteric surfactant having the following structure

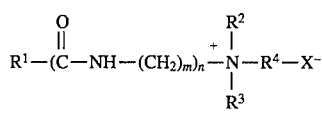

$$R^1-(C-NH-(CH_2)_m)_n-\overset{R^2}{\underset{R^3}{\overset{+}{N}}}-R^4-X^-$$

wherein $R^1$ is unsubstituted, saturated or unsaturated, straight or branched chain alkyl having from about 9 to about 22 carbon atoms; m is an integer from 1 to about 3; n is 0 or 1; $R^2$ and $R^3$ are independently selected from alkyl having from 1 to about 3 carbon atoms and monohydroxyalkyl having from about 1 to about 3 carbon atoms; $R^4$ is selected from saturated or unsaturated alkyl having from 1 to about 5 carbon atoms and saturated or unsaturated monohydroxyalkyl having from 1 to about 5 carbon atoms; X is selected from the group consisting of $CO_2$, $SO_3$, and $SO_4$; and pharmaceutically acceptable salts of the foregoing compounds;

(b) from about 0.1% to about 20% by weight of an anionic surfactant, (c) from about 0.1% to about 15% by weight of a cationic surfactant, and (d) from about 45% to about 99.7% by weight water, comprising the steps of:

(i) combining an aqueous solution of said amphoteric surfactant and an aqueous solution of said anionic surfactant to form an aqueous dispersion of a complex of said amphoteric and said anionic surfactant, and (ii) combining said aqueous dispersion of said complex with an aqueous solution of said cationic surfactant.

All percentages and ratios used herein are by weight of the total composition and all measurements made are at 25° C. or room temperature, unless otherwise designated. All weight percentages, unless otherwise indicated, are on an actives weight basis. The invention hereof can comprise, consist of, or consist essentially of, the essential as well as the optional ingredients and additional components described herein.

DETAILED DESCRIPTION OF THE INVENTION

The compositions of the present invention are useful for application to human skin. These compositions are useful for conditioning the skin, for desquamating the skin, for treating dry skin, for delivering active ingredients to the skin, and in the cleansing embodiments, for cleansing the skin without over-drying or irritating the skin.

Without being limited by theory it is believed that the amphoteric surfactant of these compositions can potentially complex with both the anionic and cationic surfactant components. Additionally, the anionic surfactant can potentially complex with the cationic surfactant component. These multiple complexes tend to be viscous and lubricious leading to a soft or smooth, elegant skin feel. These complexes are also believed to be highly stable relative to the individual surfactant components. These complexes are useful for aiding in the delivery to the skin of any active ingredients which can be present in the compositions. In the case of a cleansing composition, these complexes tend to deposit out from the composition, thereby helping to carry any active ingredients to the skin's surface, while leaving a soft, smooth skin feel. Because the postulated complexes can contain various combinations of amphoteric, anionic, and cationic surfactants, these complexes are also effective for cleansing the skin and for promoting the desquamation process. Because the charges on the individual surfactants are complexed, the surfactants are tendered less harsh and irritating to the skin versus the free surfactants.

The compositions of the present invention can be formulated into a wide variety of product types including, but not limited to creams, lotions, mousses, sprays, "rinse-off" cleansers, "water-less" cleansers, bars, gels, and the like. The term "rinse", as used herein, means that the composition is in a form that can be used in a cleansing process whereby the composition is ultimately rinsed or washed from the skin with water to complete the cleansing process. The term "water-less", as used herein, means that the composition is in the form that can be used in a cleansing process without water whereby the composition is typically removed by wiping with a device such as a cotton ball, a cotton pad, a tissue, a towel, and the like.

The term "pharmaceutically-acceptable," as used herein, means that the compositions and components thereof so described are of sufficiently high purity and are suitable for use in contact with human skin and tissues without undue toxicity, irritation, incompatibility, instability, allergic response, and the like.

The term "pharmaceutically-acceptable salts," as used herein means any of the commonly-used salts that are suitable for use in contact with human skin and tissues without undue toxicity, irritation, incompatibility instability, allergic response, and the like.

AMPHOTERIC SURFACTANT

The composition of the present invention comprise from about 0.1% to about 20%, more preferably from about 0.2% to about 10%, and most preferably from about 0.5% to about 5% of an amphoteric surfactant.

The term "amphoteric surfactant," as used herein, is also intended to encompass zwitterionic surfactants, which are well known to formulators skilled in the art as a subset of amphoteric surfactants.

A wide variety of amphoteric surfactants can be used in the compositions of the present invention. Particularly useful are those which are broadly described as drivatives of aliphatic secondary and tertiary amines, preferably wherein the nitrogen is in a cationic state, in which the aliphatic radicals can be straight or branched chain and wherein one of the radical contains an ionizable water solubilizing group, e.g., carboxy, sulfonate, sulfate, phosphate, or phosphonate.

Nonlimiting examples of amphoteric surfactant useful in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Preferred amphoteric or zwitterionic surfactants are the betaines, sultaines, and hydroxysultaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, stearyl betaine, lauryl dimethyl sulfoethyl betaine, lauryl bis-(2- hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc).

Preferred for use herein are amphoteric surfactants having the following structure:

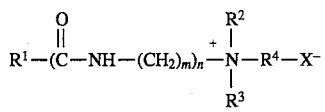

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected from the group consisting of $CO_2$, $SO_3$ and $SO_4$; $R^4$ is selected from the group consisting of saturated or unsaturated, straight or branched chain alkyl, unsubstituted or monosubstituted with hydroxy, having from 1 to about 5 carbon atoms. When X is a $CO_2$, $R^4$ preferably has 1 or 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include the following compounds:

Cetyl dimethyl betaine (this material also has the CTFA designation cetyl betaine)

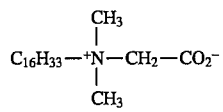

Cocamidopropylbetaine

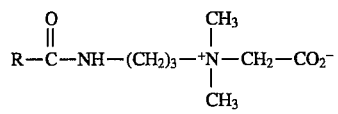

wherein R has from about 9 to about 13 carbon atoms

Cocamidopropyl hydroxy sultaine

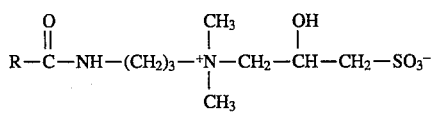

wherein R has from about 9 to about 13 carbon atoms,

Stearyl dimethyl betaine

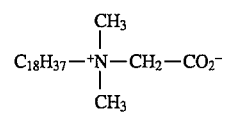

and, Behenyl Betaine

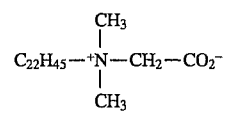

Preferred amphoteric surfactants of the present invention include cetyl dimethyl betaine, cocoamidopropyl betaine, stearyl dimethyl betaine, and cocoamidopropyl hydroxy sultaine. Still more preferred are cetyl dimethyl betaine, stearyl dimethyl betaine, and cocamidopropyl betaine. Most preferred is cetyl dimethyl betaine.

Examples of other useful amphoteric surfactants are alkyliminoacetates, and iminodialkanoates and aminoalkanoates of the formulas $RN[CH_2)_mCO_2M]_2$ and $RNH(CH_2)_mCO_2M$ where m is from 1 to 4, R is a $C_8$–$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercial available as Monaquat PTC, from Mona Corp.).

ANIONIC SURFACTANT

The compositions of the present invention comprise from about 0.1% to about 20%, more preferably from about 0.2% to about 10%, and most preferably from about 0.5% to about 5% of an anionic surfactant.

Nonlimiting examples of anionic surfactants useful in the compositions of the present invention are disclosed in McCutcheon's, *Detergents and Emulsifiers*, North American edition (1986), published by allured Publishing Corporation; McCutcheon's, *Functional Materials*, North American Edition (1992); and U.S. Pat. No. 3,929,678, to Laughlin et al., issued Dec. 30, 1975 all of which are incorporated by reference herein in their entirety.

A wide variety of anionic surfactants are useful herein. Nonlimiting examples of anionic surfactants include the alkoyl isethionates, and the alkyl ether sulfates. The alkoyl isethionates typically have the formula RCO—$OCH_2CH_2SO_3M$ wherein R is alkyl or alkenyl of from about 10 to about 30 carbon atoms, and M is a water-soluble cation such as ammonium, sodium, potassium and triethanolamine. Nonlimiting examples of these isethionates include those alkoy isethonates selected from the group consisting of ammonium cocoyl isethionate, sodium cocoyl isethionate, sodium lauroyl isethionate, sodium stearoyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

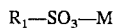

wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials include the sarcosinates nonlimiting examples of which include sodium lauroyl sarcosinate, sodium cocyl sarcosinate, and ammonium lauroyl carcosinate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, caster oil, tallow, lard, etc.) The fatty acids can also be synthetically prepared. Soaps are described in more detail in U.S. Pat. No. 4,557,853, cited above.

Other anionic materials include phosphates such as monoalkyl, dialkyl, and trialkylphosphate salts.

Other anionic materials include alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

Nonlimiting examples of preferred anionic surfactants useful herein include those selected from the group consisting of sodium lauryl sulfate, ammonium lauryl sulfate, ammonium cetyl sulfate, sodium cetyl surface, sodium stearyl sulfate, ammonium cocoyl isethionate, sodium lauroyl isethionate, sodium lauroyl sarcosinate, and mixtures thereof.

Especially preferred for use herein is sodium lauryl sulfate.

CATIONIC SURFACTANT

The compositions of the present invention comprise from about 0.1% to about 15%, more preferably from about 0.2% to about 10%, and most preferably from about 0.5% to about 5% of a cationic surfactant.

Nonlimiting examples of cationic surfactants useful in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonlimiting examples of cationic surfactants useful herein include cationic ammonium salts such as those having the formula:

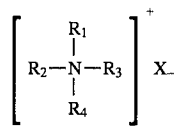

wherein $R_1$, is selected from an alkyl group having from about 12 to about 22 carbon atoms, or aromatic, aryl or alkaryl groups having from about 12 to about 22 carbon atoms; $R_2$, $R_3$, and $R_4$ are independently selected from hydrogen, an alkyl group having from about 1 to about 22 carbon atoms, or aromatic, aryl or alkaryl groups having from about 12 to about 22 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described in the previous paragraph.

More preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Alternatively, other useful cationic surfactants include amino-amides, wherein in the above structure $R_1$ is alternatively $R_5CO-(CH_2)_n-$, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof. Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixture of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammoniums nitrate, di(coconutalkyl)dimethyl ammonium chloride, di(coconutalkyl)dimethyl ammonium bromide tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Preferred cationic surfactants useful herein include those selected from the group consisting of dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, and mixtures thereof.

WATER

The compositions of the present invention comprise from about 45% to about 99.7%, more preferably from about 60% to about 95%, and most preferably from about 70% to about 90% of water. The exact level of water will depend upon the form of the product and the desired moisture content.

ADDITIONAL COMPONENTS

The compositions of the present invention can comprise a wide range of additional components. The *CTFA Cosmetic Ingredient Handbook*, Second Edition, 1992, which is incorporated by reference herein in its entirety, describes a wide variety of cosmetic and pharmaceutical ingredients commonly used in the skin care industry, which are suitable for use in the compositions of the present invention. Nonlimiting examples of functional classes of ingredients are described at page 537 of this reference. Examples of these functional classes include: absorbents, abrasives, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include emulsifiers, sequestrants, skin sensates, and the like.

Nonlimiting examples of these additional components cited in the *CTFA Cosmetic Ingredient Handbook*, as well as other materials useful herein, include the following: vitamins and derivatives thereof [e.g., vitamin C, Vitamin A (i.e. retinoic acid), retinol, esters of retinoic acid, esters of retinol, retinoids, pathenol, pathenol esters, tocopherol, tocopherol esters, and the like]; oil or sebum control agents such as clays silicones and drug actives; sunscreening agents; other silicone material such as dimethiconol, dimethicone copolyol, and amodimethicone, and the like; antioxidants; anti-microbial agents; preservatives; emulsifiers; polyethyleneglycols and polypropyleneglycols; polymers for aiding the film-forming properties and substantivity of the compositions (such as a copolymer of eicosene and vinyl pyrrolidone, an example of which is available from GAF Chemical Corporation as Ganex® V-220); preservatives for maintaining the antimicrobial integrity of the compositions; anti-acne medicaments (e.g., resorcinol, sulfur, salicylic acid, erythromycin, zinc, and the like); skin bleaching (or lightening) agents including but not limited to hydroquinone, kojic acid; antioxidants; chelators and sequestrants; thickening agents such as carbomers (homopolymers of acrylic acid crosslinked with an allyl ether of pentaerythritol or an ally ether of sucrose), crosslinked and noncrosslinked nonionic and cationic polyacrylamides [e.g., Salcare® SC92 which has the CTFA designation polyquaternium 32 (and) mineral oil, and Salcare® SC95 which has the CTFA designation polyquaternium 37 (and) mineral oil (and) PPG-1 trideceth-6, and the nonionic Seppi-Gel polyacrylamides available from Seppic Corp.]; proteins and peptides; enzymes; ceramides; aesthetic components such as fragrances, pigments, colorings, essential oils, skin senates, astringents, skin soothing agents, skin healing agents and the like, [nonlimiting examples of these aesthetic components include clove oil, menthol, camphor, eucalyptus oil, eugenol, menthyl lactate, witch hazel distillate, bisabolol, dipotassium glycyrrhizinate and the like]; and skin conditioning agents such as urea and glycerol, and also the propoxylated glycerols described in U.S. Pat. No. 4,976,953, or Orr et al., issued Dec. 11, 1990, which is incorporated by reference herein in its entirety.

Some of these additional ingredients are described in more detail below.

ACTIVE INGREDIENTS

The compositions of the present invention comprise a safe and effective amount of one or more active ingredients of pharmaceutically-acceptable salts thereof.

The term "safe and effective amount" as used herein, means an amount of an active ingredient high enough to modify the condition to be treated or to deliver the desired skin benefit, but low enough to avoid serious side effects, at a reasonable benefit to risk ratio within the scope of sound medical judgement. What is a safe and effective amount of the active ingredient will vary with the specific active, the ability of the active to penetrate through the skin, the age, health condition, and skin condition of the user, and other like factors.

Typically, the active ingredients of the present invention comprise from about 0.001% to about 20%, preferably from a bout 0.01% to about 15%, and more preferably from about 0.025% to about 10% by weight of the composition.

The active ingredients useful herein can be categorized by their therapeutic benefit or their postulated mode of action. However, it is to be understood that the active ingredients useful herein can in some instances provide more than one therapeutic benefit or operate via more than one mode of action. Therefore, classifications herein are made for the sake of convenience and are not intended to limit the active ingredient to that particular application or applications listed. Also, pharmaceutically-acceptable salts of these active ingredients are useful herein. The following active ingredients are useful in the compositions of the present invention.

Anti-Acne Actives: Examples of useful anti-acne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cystein; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives: Examples of antiwrinkle and anti-skin atrophy actives include retinoic acid and its derivatives (e.g., cis and trans); retinol, retinyl esters, salicylic acid and derivatives thereof; sulfur-containing D and L amino acids and their derivatives and salts, particularly the N-acetyl derivatives, a preferred example of which is N-acetyl-L-cystein; thiols, e.g., ethane thiol; alpha-hydroxy acids, e.g. glycolic acid, and lactic acid; phytic acid, lipoic acid; lysophosphatidic acid, and skin peel agents (e.g., phenol and the like).

Non-Steroidal Anti-Inflammatory Actives (NSAIDS); Examples of NSAIDS include the following categories: propionic acid derivatives; acetic acid derivatives; fenamic acid derivatives; biphenylcarboxylic acid derivatives; and oxicams. All of these NSAIDS are fully described in U.S. Pat. No. 4,985,459 to Sunshine et al., issued Jan. 15, 1991, incorporated by reference herein in its entirety. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, microprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics: Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Artificial Tanning Agents and Accelerators: Examples of artificial tanning agents and accelerators include dihydroxyacetone, tyrosine, tyrosine esters such as ethyl tyrosinate, and phospho-DOPA.

Antimicrobial and Antifungal Actives: Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin steaerate, amikacin sulfate, doxycycline hydrochloride, capreomycin sulfate, chlorhexidine gluconate, chlorhexidine hydrochloride, chlortetracycline, hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mendelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xyleneol, nystatin, tolnaftate and clotrimazole.

Sunscreen Actives: Also useful herein are sunscreening actives. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetic Science and Technology*, all of which are incorporated herein by reference in their entirety. Nonlimiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropy dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreening agents disclosed therein have, in a single molecule, two distinct chromophore moieties which exhibit different ultraviolet radiation absorption spectra. One of the chromophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens. Especially preferred examples of these sunscreens include those selected from the group consisting of 4-N,N-(2-ethylhexyl)methylaminobenzoic acid ester of 2,4-dihydroxybenzophenone, 4-N,N-(2-ethylhexyl)-methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy)dibenzoylmethane, and mixtures thereof. Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Register*, Vol. 43, No. 166, pp. 38206–38269, Aug. 25, 1978, which is incorporated herein by reference in its entirety.

Preferred examples of actives useful herein include those selected from the group consisting of salicylic acid, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbailide, octopirox, lidocaine hydrochloride, clotrimazole, miconazole, neocycin sulfate, p-aminobenzoic acid, 2-phenylbenzimidazole-5-sulfonic acid, dihydroxyacetone, and mixtures thereof.

More preferred examples of actives useful herein include those selected from the group consisting of salicylic acid, benozyl peroxide, acetyl salicylic acid, cis-retinoic acid, trans-retinoic acid, retinol, phytic acid, N-acetyl-L-cystein, lipoic acid, azelaic acid, tetracycline, ibuprofen, naproxen acetominophen, hydrocortisone, resorcinol, phenoxyethanol, phenoxypropanol, phenoxyisopropanol, 2,4,4'-trichloro-2'-hydroxy diphenyl ether, 3,4,4'-trichlorocarbanilide, octopirox, 2-phenylbenzimidazole-5-sulfonic acid, dihydroxyacetone, and mixtures thereof.

Most preferred examples of actives useful herein include those selected from the group consisting of salicyclic acid, benzoyl peroxide, cis-retinoic acid, trans-retinoic acid, retinol, phytic acid, N-acetyl L-cysteine, azelaic acid, lipoic acid, resorcinol, lactic acid, glycolic acid, ibuprofen, naproxen, hydrocortisone, phenoxyethanol, phenoxypropanol, phenoxyisopropanol, 2,4,4'-trichloro-2'-hydroxy diphenyl ether, 3,4,4'-trichlorocarbanilide, 2-ethylhexyl p-methoxycinnamic acid, oxybenzone, 2-phenylbenzimidazole-5-sulfonic acid, dihydroxyacetone, and mixtures thereof.

HUMECTANTS AND MOISTURIZERS

The compositions of the present invention can also comprise one or more humectants or moisturizers. A variety of these materials can be employed and each can be present at a level of from about 0.1% to about 20%, more preferably from about 0.5% to about 15%, and most preferably from about 1% to about 10%. Nonlimiting examples of humectants include materials selected from the group consisting of guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof.

Also, useful are propoxylated glycerols as described in U.S. Pat. No. 4,976,953, to Orr et al., issued Dec. 11, 1990, which is incorporated by reference herein in its entirety.

An especially preferred humectant for use herein is glycerol.

INSOLUBLE PARTICLES

The compositions of the present invention can comprise from about 0.1% to about 20%, more preferably from about 0.25% to about 15%, and most preferably from about 0.5% to about 10%, based on the weight of the total composition, of insoluble particles which are useful for enhancing the cleansing effect, when the compositions of the present invention are in the form of a cleansing composition.

The term "insoluble", as used herein, means that the particles are essentially insoluble in the compositions of the present invention. In particular, the insoluble particles should have a solubility less than about 1 gram per 100 grams of composition at 25° C., preferably less than about 0.5 grams per 100 grams of composition at 25° C., and more preferably less than about 0.1 grams per 100 grams of composition at 25° C.

Useful herein are both micronized and conventional size insoluble particles. The micronized particles, for the most part, are of a size that is below the tactile threshold and are essentially nonabrasive to the skin. The conventional size particles are tactilely perceptible and are added for the scrubbing and abrasive effect which they provide.

The micronized particles have a mean particle size diameter and particle size distribution such that they are below the tactile perception threshold of most users, and yet are not so small as to be ineffective for aiding in oil, dirt, and debris (e.g., make-up) removal. It is found herein that particles having a mean particle size diameter greater than bout 75 microns are tactilely perceived during the cleansing process and it is important to minimize the amount of these larger particles if it is desired that the particles not be felt by the user. Conversely, it is found that particles having a means particle size diameter of less than about 1 to about 5 microns are generally less effective for providing a cleansing benefit. Without being limited by theory, it is believed that the micronized cleansing particles should be of a size that is on the order of the thickness of the dirt, oil, or debris layer to be cleaned away. This layer is believed to be on the order of a few microns in thickness in most instance. It is therefore found in the present invention that the micronized particles should have a mean particle size diameter from about 1 to about 75 microns, more preferably from about 15 to about 60 microns, and most preferably from about 20 to about 50 microns, so as to provide effective cleansing without being tactilely perceptible. Particles having a wide range of shapes, surface characteristics, and hardness characteristics can be utilized herein provided the particle size requirements are met. Micronized particles of the present invention can be derived from a wide variety of materials including those derived from inorganic, organic, natural, and synthetic sources. Nonlimiting examples of these materials include those selected from the group consisting of almond meal, alumina, aluminum oxide, aluminum silicate, apricot seed powder, attapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e. polytetrafluoroethylene), polyhalogenated olefins, pumice rice bran, rye flour, cericite, silica, silk, sodium bicarbonate, sodium silicoaluminate, soy flour synthetic hectorite, talc, tin oxide, titanium disoide, tricalcium phosphate, walnut shell powder, wheat bran, wheat flour, wheat starch, zirconium silicate, and mixtures thereof. Also useful are micronized particles made from mixed polymers (e.g., copolymers terpolymers, etc.), such as polyethlene/polypropylene copolymer, polyethylene/propylene/isobutylene copolymer, polyethlene/styrene copolymer, and the like. Typically, the polymeric and mixed polymeric particles are treated via an oxidation process to destroy impurities and the like. The polymeric and mixed polymeric particles can also optionally be crosslinked with a variety of common crosslinking agents, nonlimiting examples of which include butadiene, divinyl benzene, methylenebisacrylamide, allyl ethers of sucrose, allyl ethers of pentaerythritol, and mixtures thereof. Other examples of useful micronized particles include waxes and resins such as paraffins, carnuba wax, ozekerite wax, candellila wax, urea-formaldehyde resins, and the like. When such waxes and resins are used herein it is important that these materials are solids at ambient and skin temperatures.

Among the preferred water-insoluble, micronized particulate materials useful herein are the synthetic polymeric particles selected from the group consisting of polybutylene, polyethylene, polyisobutylene, polymethylstyrene, polypropylene, polystyrene, polyurethane, nylon, teflon, and mixtures thereof. Most preferred are polyethylene and polypropylene micronized particles, with the oxidized versions of these materials being especially preferred. Examples of commercially available particles useful herein include the ACumist™ micronized polyethylene waxes available from Allied Signal (Morristown, N.J.) available as the A, B, C, and D series in a variety of average particle sizes ranging from 5 microns to 60 microns. Preferred are the ACumist™ A-25, A-30, and A-45 oxidized polyethylene particles having a mean particle size of 25, 30, and 45 microns, respectively. Examples of commercially available polyproylene particles include the Porpyltex series available from Micro Powders (Dartek).

The conventional size insoluble particles are well-known to formulation chemists in the art. These particles typically have larger particle sizes than the micronized particles described herein. These particles generally have an average size diameter that is about 75 microns or greater, which is above the tactile threshold described above. These conventional size particles typically have average particles sizes ranging up to about 400 microns and larger. These particles can be made from the same materials as for the micronized particles just described. Among the preferred conventional size particulate materials useful herein are the synthetic polymeric particles selected from the group consisting of polybutylene, polyethylene, polyisobutylene, polymethylstyrene, polyethylene and polypropylene micronized particles, with the oxidized versions of these materials being especially preferred. An example of a commercially available conventional size particle useful herein is ACuscrub™51, available from Allied Signal (Morristown, N.J.) having a mean particle size of about 125 microns.

ADDITIONAL SURFACTANTS

The compositions of the present invention, in addition to the required surfactant materials, can comprise additional surfactant materials. Especially useful for noninoic surfactants.

Nonlimiting examples of nonionic surfactants for use in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Among the nonionic surfactants that are useful herein are those that can be broadly defined as condensation products of long chain alcohols, e.g. C8-30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8-C30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8-C20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel).

Other useful nonionic surfactants include the condensation products of alkylene oxides with fatty acids (i.e. alkylene oxide esters of fatty acids). These materials have the general formula $RCO(X)_nOH$ wherein R is a C10-30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 1 to about 100. Other nonionic surfactants are the condensation products of alkylene oxides with 2 moles of fatty acids (i.e. alkylene oxide diesters of fatty acids). These materials have the general formula $RCO(X)_nOOCR$ wherein R is a C10-C30 alkyl group, X is —OCH$_2$CH$_2$—(i.e. derived from ethylene glycolor oxide) or —OCH$_2$CHCH$_3$-(i.e. derived from propylene glycol or oxide), and n is an integer from about 1 to about 100. Other nonionic surfactants are the condensation products of alkylene oxides with fatty alcohols (i.e. alkylene oxide ethers of fatty alcohols). These materials have the general formula $R(X)_nOR'$ wherein R is a C10-C30 alkyl group, X is —OCH$_2$CH$_2$—(i.e. derived from ethylene glycol or oxide) or —OCH$_2$CHCH$_3$—(i.e. derived from propylene glycol or oxide), and n is an integer from about 1 to about 100 and $R^1$ is H or a C10-30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_nOR'$ wherein R and R' are C10-30 alkyl groups, X is —OCH$_2$CH$_2$ (i.e. derived from ethylene glycol or oxide) or —OCH$_2$CHCH$_3$—(derived from propylene glycol or oxide), and n is an integer from about 1 to about 100. Nonlimiting examples of these alkylene oxide derived nonionic surfactants include ceteth-1, ceteth-2, ceteth-6, ceteth-10, ceteth-12, ceteareth-2, ceteareth-6, ceteareth-10, ceteareth-12, steareth-1, steareth-2, steareth-6, steareth-10, steareth-12, steareth-21, PEG-2 stearate, PEG-4 stearate, PEG-6 stearate, PEG-10 stearate, PEG-12 stearate, PEG-20 glyceryl stearate, PEG-80 glyceryl tallowate, PPG-10 glycerl stearate, PEG-30 glyceryl cocoate, PEG-80 glyceryl cocoate, PEG-200 glycerl tallowate, PEG-8 dilaurate, PEG-10 distearate, and mixtures thereof.

Still other useful nonionic surfactants include polyhydroxy fatty acid amide surfactants corresponding to the structural formula:

wherein: $R^1$ is H, $C_1-C_4$ alkyl, 2-hydroxyethyl, 2-hydroxypropyl, preferably $C_1-C_4$ alkyl, more preferably methyl or ethyl, most preferably methyl; $R^2$ is $C_5-C_{31}$ alkyl or alkenyl, preferably $C_7-C_{19}$ alkyl or alkenyl, more preferably $C_9-C_{17}$ alkyl or alkenyl, most preferably $C_{11}-C_{15}$ alkyl or alkenyl; and Z is a polydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polydroxy fatty acid amides are disclosed, for example, in G.B. Patent Specification 809, 060, published Feb. 18, 1959, by Thomas Hedley & Co., Ltd.; U.S. Pat. No. 2,965,576, to E. R. Wilson, issued Dec. 10, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

EMULSIFIERS

The compositions herein can comprise various emulsifiers. These emulsifiers are useful for emulsifying the various carrier components of the compositions herein. Suitable emulsifiers can include any of a wide variety of nonionic, cationic, anionic, and zwitterionic emulsifiers disclosed in the prior patents and other references. See McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

The emulsifiers can be used individually or as a mixture of two or more and can comprise from about 0.1% to about 10%, more preferably from about 0.15% to about 7%, and most preferably from about 0.2% to about 5% of the compositions of the present invention.

OILS

The compositions of the present invention can comprise from about 0.25% to about 40%, preferably from about 0.5% to about 25%, and more preferably from about 0.75% to about 15% of an oil selected from the group consisting of mineral oil, petrolatum, C7-C40 branched chain hydrocarbons, C1-C30 alcohol esters of C1-C30 carboxylic acids, C1-C30 alcohol esters of C2-C30 dicarboxylic acids, monoglycerides of C1-C30 carboxylic acids, diglycerides of C1-C30 carboxylic acids, triglycerides of C1-C30 carboxylic acids, ethylene glycol monoesters of C1-C30 carboxylic acids, ethylene glucol diesters of C1-C30 carboxylic acids, propylene glycol monoesters of C1-C30 carboxylic acids, propylene glucol diesters of C1-C30 carboxylic acids, C1-C30 carboxylic acid monesters and polyesters of sugars, polydialkylsiloxanes, polydiarylsiloxanes, polyalkarylsiloxanes, cyclomethicones having 3 to 9 silicon atoms, vegetable oils, hydrogenated vegetable oils, polypropylene glycols, polypropylene glycol C4-C20 alkyl ethers, di C8-C30 alkyl ethers, and mixtures thereof.

The oil materials generally having low solubility in water, generally less than about 1% by weight at 25° C. Nonlimiting examples of suitable oil components include, but are not limited to, the following materials. Some of these materials are further described in U.S. Pat. No. 4,919,934, to Deckner et al., issued Apr. 24, 1990, which is incorporated herein by reference in its entirety.

Mineral oil, which is also known as petrolatum liquid, is a mixture of liquid hydrocarbons obtained from petroleum. See *The Merck Index*, Tenth Edition, Entry 7048, p. 1033 (1983) and International Cosmetic Ingredient Dictionary, Fifth Edition, vol. 1, p. 415–417 (1993), which are incorporated by reference herein in their entirety.

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, *Drug. Cosmet. Ind.*, 89, 36–37, 76, 78–80, 82 (1961); and International Cosmetic Ingredient Dictionary, Fifth Edition, vol. 1, p. 537 (1993), which are incorporated by reference herein in their entirety.

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). Also useful are the C7-C40 isoparaffins, which are C7-C40 branched hydrocarbons.

Useful oils include C1-C30 alcohol esters of C1-C30 carboxylic acids and of C2-C30 dicarboxylic acids, including straight and branched chain materials as well as aromatic derivatives. Also useful are esters such as monoglycerides of C1-C30 carboxylic acids, deglycerides of C1-C30 carboxylic acids, triglycerides of C1-C30 carboxylic acids, ethylene glycol monoesters of C1-C30 carboxylic acids, ethylene glycol diesters of C1-C30 carboxylic acids, propylene glycol monoesters of C1-C30 carboxylic acids, and propylene glycol diesters of C1-C30 carboxylic acids. Straight chain, branched chain and aryl carboxylic acids are included herein. Also useful are propoxylated and ethoxylated drivatives of these materials. Nonlimiting examples include diisopropyl sebacate, diisopropyl adipate, isopropyl myristate, isopropyl palmitate, myristyl propionate, ethylene glycol distearate, 2-ethylhexyl palmitate, isodecyl neopentanoate, $C_{12-15}$ alcohols benzoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, caprilic/capric triglyceride, PEG-6 caprylic/capric triglyceride, PEG-8 caprylic/capric triglyceride, and mixtures thereof.

Also useful are various C1-C30 monesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, surcrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboyxlic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behanate in a 2:6 molar ratio; and the octaester of sucrose wherein the esterifying carboxylic acid moieties are laurate, linoleate and behenate in a 1:3:4 molar ratio. A preferred solid material is surcrose polyester in which the degree of esterification is 7–8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Silicones such as polydialkylsiloxanes, polydiarylsiloxanes, polyalkarylsiloxanes, and cyclomethicones having 3 to 9 silicon atoms are useful oils. These silicones include both volatile and nonvolatile materials. These silicones are disclosed in U.S. Pat. No. 5,069,897, to Orr, issued Dec. 3, 1991, which is incorporated by reference herein in its entirety. The polyalkylsiloxanes include, for example, polyalkylsiloxanes with viscosities of from about 0.5 to about 100,000 centistokes at 25° C. Such polyalkylsiloxanes correspond to the general chemical formula $R_3SiO[R_2SiO]_xSiR_3$ wherein R is an alkyl group (preferably R is methyl or ethyl, more preferably methyl) and x is an integer from 0 to about 500, chosen to achieve the desired molecular weight. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful as emollients herein include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Cyclic polyalkylsiloxanes useful herein include those corresponding to the general chemical formula $[SiR_2—O]_n$ wherein R is an alkyl group (preferably R is methyl or ethyl, more preferably methyl) and n is an integer from about 3 to about 9, more preferably n is an integer from about 3 to about 7, and most preferably n is an integer from about 4 to about 6. When R is methyl, these materials are typically referred to as cyclomethicones. Commercially available cyclomethicones include Dow Corning° 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), and Dow Corning® 245 fluid having a viscosity of 4.2 centistokes and a boiling point of 205° C., which primarily contains a mixture of the cyclomethicone tetramer and pentamer (i.e. n=4 and 5), Dow Corning® 345 fluid having a viscosity of 4.5 centistokes and a boiling point of 217°, which primarily contains a mixture of the cyclomethicone tetramer, pentamer, and hexamer (i.e. n=4, 5, and 6). Also useful are materials such as trimethylsiloxysilicate, which is a polymeric material corresponding to the general chemical formula $[(CH_2)_3SiO_{1/2}]_x[SiO_2]y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning®1401, 1402, and 1403 fluids). Also useful herein are polyalkylaryl siloxanes, with polymethyphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation).

Vegetable oils and hydrogenated vegetable oils are also useful herein. Examples of vegetable oils and hydrogenated vegetable oils include safflower oil, caster oil, coconut oil, cottenseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated caster oil, hydrogenated coconut oil, hydrogenated cottenseed oil, hydrogenated menhaden oil, hydrogenated palm kernel oil, hydrogenated palm oil, hydrogenated peanut oil hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are polyproylene glycols, C4-C20 alkyl ethers of polypropylene glycols, C1-C20 carboxylic acid esters of polypropylene glycols, and di-C8-C30 alkyl ethers. Nonlimiting examples of these materials include PPG-14 butyl ether, PPG-15 stearyl ether, PPG-9, PPG-12, PPG-15, PPG-17, PPG-20, PPG-26, PPG-30, PPG-34, dioctyl ether, dodecyl octyl ether, and mixtures thereof.

METHOD OF FORMING THE COMPLEXES

The complexes that are believed to be formed from the amphoteric, anionic, and cationic surfactants of the present invention are preferably preprepared by the following procedures.

The amphoteric and anionic surfactants are first combined in aqueous solution, thereby forming that is believed to be a dispersion of the complex between these two materials. This dispersion is then combined directly with an aqueous solution of the cationic surfactant. Alternatively, this dispersion can be added directly to a composition already containing the desired cationic surfactant.

METHODS OF TREATING THE SKIN

The present invention also relates to methods wherein an effective amount of the composition of the present invention is applied to the skin. These compositions are useful for conditioning and treating dry skin and for providing active ingredients to the skin. A wide range of quantities of the compositions of the present invention can be used. Quantities which are typically applied can range from about 0.1 mg/cm$^2$ to about 25 mg/cm$^2$.

In further embodiments, the compositions of the present invention are useful for personal cleansing, especially for cleansing of the face and neck areas. Typically, a suitable or effective amount of the cleansing composition is applied to the area to be cleansed. Alternatively, a suitable amount of the cleansing composition can be applied via intermediate application to a washcloth, sponge, pad, cotton ball or other application device. If desired, the area to be cleansed can be premoistened with water. It has been found that the compositions of the present invention can be combined with water during the cleansing process and rinsed-off from the skin. Alternatively, the composition can be used along and wiped-off from the skin using a pad, cotton ball, tissue, or other like device. The cleansing process is typically a two-step process involving application of the composition followed either by rinsing of the produce with water or wiping without the use of water. Generally, an effective amount of composition to be used will depend upon the needs and usage habits of the individual.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Example 1

A leave-on lotion composition containing benzoyl peroxide is prepared by combining the following ingredients using conventional mixing techniques.

| Ingredients | Weight Percent |
| --- | --- |
| Phase A | |
| Water | QS 100 |
| Glycerin | 4.00 |
| Disodium EDTA | 0.10 |
| Carbomer | 0.60 |
| Acrylates/C10–30 Alkylacrylates Crosspolymer | 0.05 |
| Phase B | |
| Stearyl Alcohol | 2.25 |
| Cetyl Alcohol | 2.25 |
| Steareth-100 | 0.50 |
| Distearyl Dimethyl Ammonium Chloride | 0.20 |
| Phase C | |
| Triethanolamine | 0.50 |
| Phase D | |
| Benzoyl Peroxide | 2.50 |
| Phase E | |
| Cetyl Dimethyl Betaine | 1.00 |
| Sodium Lauryl Sulfate | 0.50 |

In a suitable vessel, the Phase A ingredients are heated with stirring to about 75° C. In a separate vessel, the Phase B ingredients are heated with stirring to about 75° C. Phase B is then added to Phase A with mixing. Next Phase C is added with mixing. Next, the mixture is cooled to 35° C. Next the benzoyl peroxided is added with mixing. In a separate vessel, the Phase E ingredients are combined and added to the remaining mixture with stirring.

The resulting leave-on composition is useful for preventing and treating acne while being mild to the skin.

Alternatively, a composition is prepared in which the cetyl dimethyl betaine is replaced with stearyl dimethyl betaine.

Example 2

A personal cleanser composition containing salicylic acid is prepared by combining the following ingredients using conventional mixing techniques.

| Ingredients | Weight Percent |
| --- | --- |
| Phase A | |
| Water | QS 100 |
| Glycerin | 3.00 |
| Disodium EDTA | 0.01 |
| Phase B | |
| PPG-15 Stearyl Ether | 4.00 |
| Stearyl Alcohol | 2.88 |
| Salicylic Acid | 2.00 |
| Distearyl Dimonium Chloride | 1.50 |
| Cetyl Alcohol | 0.80 |
| Steareth-21 | 0.50 |
| Behenyl Alcohol | 0.32 |
| PPG-30 | 0.25 |
| Steareth-2 | 0.25 |
| Phase C | |
| Oxidized Polyethylene Beads[1] | 1.00 |
| Fragrance | 0.27 |
| Phase D | |
| Cocamidopropyl Betaine | 2.00 |
| Sodium Lauryl Sulfate | 1.00 |

[1] Available as Acucscrub ™ 51 from Allied Signal Corporation.

In a suitable vessel, the Phase A ingredients are heated with stirring to about 75° C. In a separate vessel, the Phase B ingredients are heated with stirring to about 75° C. Phase B is then added to Phase A with mixing. Next, the oxidized polyethylene beads are added slowly with mixing to prevent agglomeration. Next the fragrance is added with mixing. Next, the mixture is cooled to 35° C. In a separate vessel, the Phase D ingredients are combined and added to the remaining mixture with stirring (typically these ingredients are available as aqueous solutions and are combined as such).

The resulting cleansing composition is useful for cleansing the skin.

Alternatively, a composition is prepared in which the sodium lauryl sulfate is replaced with sodium lauroyl isetheonate.

Example 3

A personal cleanser is prepared by combining the following ingredients using conventional mixing techniques.

| Ingredients | Weight Percent |
|---|---|
| Phase A | |
| Water | QS 100 |
| Glycerin | 3.00 |
| Disodium EDTA | 0.10 |
| Methylparaben | 0.15 |
| Phase B | |
| PPG-15 Stearyl Ether | 4.00 |
| Stearyl Alcohol | 2.88 |
| Distearyl Dimonium Chloride | 1.50 |
| Cetyl Alcohol | 0.80 |
| Steareth-21 | 0.50 |
| Behenyl Alcohol | 0.32 |
| PPG-30 | 0.25 |
| Steareth-2 | 0.25 |
| Propylparaben | 0.10 |
| Phase C | |
| Fragrance | 0.27 |
| Menthol | 0.05 |
| Phase D | |
| Cetyl Dimethyl Betaine | 2.00 |
| Sodium Lauryl Sulfate | 1.00 |

In a suitable vessel, the Phase A ingredients are heated with stirring to about 75° C. In a separate vessel, the Phase B ingredients are heated with stirring to about 75° C. Phase B is then added to Phase A with mixing. Next the fragrance and menthol are added with mixing. Next, the mixture is cooled to 35° C. In a separate vessel, the Phase D ingredients are combined and added to the remaining mixture with stirring (typically these ingredients are available as aqueous solutions and are combined as such).

The resulting cleansing composition is useful for cleansing the skin.

Alternatively, a composition is prepared in which the menthol is eliminated and the water level is correspondingly increased.

Alternatively, a composition is prepared in which the sodium lauryl sulfate is replaced with sodium lauroyl isetheonate.

Example 4

A leave-on cream composition is prepared by combined the following ingredients using conventional mixing techniques.

| Ingredients | Weight Percent |
|---|---|
| Phase A | |
| Water | QS 100 |
| Glycerin | 5.00 |
| Disodium EDTA | 0.10 |
| Methylparaben | 0.20 |
| Phase B | |
| PPG-15 Stearyl Ether | 4.00 |
| Stearyl Alcohol | 1.44 |
| Distearyl Dimonium Chloride | 0.50 |
| Cetyl Alcohol | 0.40 |
| Steareth-21 | 0.50 |
| Behenyl Alcohol | 0.16 |
| Steareth-2 | 0.15 |
| Propylparaben | 0.10 |
| Phase C | |
| Fragrance | 0.12 |
| Phase D | |
| Cetyl Dimethyl Betaine | 1.00 |
| Sodium Lauryl Sulfate | 0.50 |

In a suitable vessel, the Phase A ingredients are heated with stirring to about 75° C. In a separate vessel, the Phase B ingredients are heated with stirring to about 75° C. Phase B is then added to Phase A with mixing. Next the fragrance is added with mixing. Next, the mixture is cooled to 35° C. In a separate vessel, the Phase D ingredients are combined and added to the remaining mixture with stirring (typically these ingredients are available as aqueous solutions and are combined as such).

The resulting leave-on cream is useful for conditioning the skin and provides a soft/smooth skin feel.

Alternatively, a composition is prepared in which the sodium lauryl sulfate is replaced with sodium lauroyl isetheonate.

Example 5

A personal cleansing gel composition is prepared by combining the following ingredients using conventional mixing techniques.

| Ingredients | Weight Percent |
|---|---|
| Phase A | |
| Water | QS 100 |
| Glycerin | 4.00 |
| Disodium EDTA | 0.10 |
| PVM/MA Decadiene Crosspolymer | 1.00 |
| Sodium Hydroxide | 0.14 |
| Methylparaben | 0.20 |
| Distearyl Dimethyl Ammonium Chloride | 0.50 |
| Phase B | |
| Cetyl Dimethyl Betaine | 0.75 |
| Sodium Lauryl Sulfate | 0.50 |

In a suitable vessel, the Phase A ingredients are mixed vigorously. In a separate vessel, the Phase B ingredients are combined and added to the remaining mixture with stirring.

The resulting cleansing gel composition is useful for cleansing the skin effectively while being mild to the skin.

Alternatively, a composition is prepared in which the cetyl dimethyl betaine is replaced with cocamidopropyl betaine.

Example 6

A leave-on lotion composition containing salicylic acid is prepared by combining the following ingredients using conventional mixing techniques.

| Ingredients | Weight Percent |
| --- | --- |
| Phase A | |
| Water | QS 100 |
| Glycerin | 3.00 |
| Tetrasodium EDTA | 0.02 |
| Phase B | |
| PPG-15 Stearyl Ether | 4.00 |
| Stearyl Alcohol | 0.75 |
| Salicylic Acid | 2.00 |
| Cetyl Alcohol | 0.75 |
| Steareth-21 | 0.45 |
| Steareth-2 | 0.05 |
| Distearyl Dimethyl Ammonium Chloride | 0.75 |
| Polyquaternium-37 (and) Mineral Oil (and) PPG-1 Trideceth-6 | 0.75 |
| Phase C | |
| Triethanolamine | 0.15 |
| Phase D | |
| Fragrance | 0.10 |
| Phase E | |
| Cetyl Dimethyl Betaine | 2.00 |
| Sodium Lauryl Sulfate | 1.00 |

In a suitable vessel, the Phase A ingredients are heated with stirring to about 75° C. In a separate vessel, the Phase B ingredients are heated with stirring to about 75° C. Phase B is then added to Phase A with mixing. Next Phase C is added with mixing. Next the fragrance is added with mixing. Next, the mixture is cooled to 35° C. In a separate vessel, the Phase E ingredients are combined and added to the remaining mixture with stirring.

The resulting leave-on composition is useful for preventing treating acne while being mild to the skin and providing a soft/smooth skin feel.

Alternatively, a composition is prepared in which the sodium lauryl sulfate is replaced with sodium lauroyl isetheonate.

Example 7

A personal cleanser composition containing salicylic acid and menthol is prepared by combining the following ingredients using conventional mixing techniques.

| Ingredients | Weight Percent |
| --- | --- |
| Phase A | |
| Water | QS 100 |
| Glycerin | 3.00 |
| Disodium EDTA | 0.01 |
| Phase B | |
| PPG-15 Stearyl Ether | 4.00 |
| Stearyl Alcohol | 2.88 |
| Salicylic Acid | 2.00 |
| Distearyl Dimonium Chloride | 1.50 |
| Cetyl Alcohol | 0.80 |
| Steareth-21 | 0.50 |
| Behenyl Alcohol | 0.32 |
| PPG-30 | 0.25 |
| Steareth-2 | 0.25 |
| Phase C | |
| Oxidized Polyethylene Beads[1] | 1.00 |
| Fragrance | 0.27 |
| Menthol | 0.05 |
| Phase D | |
| Cetyl Dimethyl Betaine | 2.00 |
| Sodium Lauryl Sulfate | 1.00 |

[1] Available as Acucsrub ™ 51 from Allied Signal Corporation.

In a suitable vessel, the Phase A ingredients are heated with stirring to about 75° C. In a separate vessel, the Phase B ingredients are heated with stirring to about 75° C. Phase B is then added to Phase A with mixing. Next, the oxidized polyethylene beads are added slowly with mixing to prevent agglomeration. Next the fragrance and menthol are added with mixing. Next, the mixture is cooled to 35° C. In a separate vessel, the Phase D ingredients are combined and added to the remaining mixture with stirring (typically these ingredients are available as aqueous solutions and are combined as such).

The resulting cleansing composition is useful for cleansing the skin.

Alternatively, a benozyl peroxide-containing composition is prepared in which the salicylic acid is replaced with 2.5% benzoyl peroxide and the water is correspondingly adjusted.

Alternatively, a composition is prepared in which the menthol is eliminated and the water level is correspondingly increased.

Alternatively, a composition is prepared in which the sodium lauryl sulfate is replaced with sodium lauroyl isetheonate.

What is claimed is:

1. A topical personal care composition comprising:
   (a) from about 0.1% to about 20% by weight of an amphoteric surfactant having the following structure

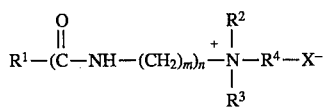

wherein $R^1$ is unsubstituted, saturated or unsaturated, straight or branched chain alkyl having from about 9 to about 22 carbon atoms; m is an integer from 1 to about 3; n is 0 or 1; $R^2$ and $R^3$ are independently selected from alkyl having from 1 to about 3 carbon atoms and monohydroxyalkyl having from 1 to about 3 carbon atoms; $R^4$ is selected from saturated or unsaturated alkyl having from 1 to about 5 carbon atoms and saturated or unsaturated monohydroxyalkyl having from 1 to about 5 carbon atoms; X is selected from the group consisting of $CO_2$, $SO_3$, and $SO_4$; and pharmaceutically acceptable salts of the foregoing compounds;
   (b) from about 0.1% to about 20% by weight of an anionic surfactant selected from the group consisting of alkyl sulfates, alkyl ether sulfates, alkoyl isethionate, and mixtures thereof,
   (c) from about 0.1% to about 15% by weight of a cationic surfactant, and
   (d) from about 45% to about 99.7% by weight water.

2. A composition according to claim 1 wherein $R^2$ and $R^3$ are selected from the group consisting of $CH_3$, $CH_2CH_2OH$ and $CH_2CH_2CH_2OH$; X is selected from $CO_2$ and $SO_3$; and m is 2 or 3.

3. A composition according to claim 2 wherein $R^2$ and $R^3$ are selected from the group consisting of $CH_3$, $CH_2CH_2OH$, and $CH_2CH_2CH_2OH$; X is selected from the group consisting of $CO_2$ and $SO_3$, and m is 2 or 3.

4. A composition according to claim 3 wherein $R^4$ has from 1 to about 3 carbon atoms when X is $CO_2$, and $R^4$ has from about 2 to about 4 carbon atoms when X is $SO_3$.

5. A composition according to claim 4 wherein $R^1$ has from 11 to about 18 carbon atoms; $R^2$ and $R^3$ are $CH_3$; and $R^4$ has 1 carbon atom when X is $CO_2$, and $R^4$ has 3 carbon atoms when X is $SO_3$.

6. A composition according to claim 5 wherein $R^4$ has 1 carbon atom, X is $CO_2$, m is 3, and n is 1.

7. A composition according to claim 5 wherein $R^4$ has 3 carbon atoms, X is $SO_3$, m is 3 and n is 1.

8. A composition according to claim 1 wherein said amphoteric surfactant is selected from the group consisting of cetyl dimethyl betaine, cocoamidopropyl betaine, cocamidopropyl hydroxy sultaine, stearyl dimethyl betaine, and mixtures thereof.

9. A composition according to claim 1 wherein the amphoteric surfactant is cetyl dimethyl betaine.

10. A composition according to claim 1 wherein said anionic surfactant is selected from the group consisting of sodium lauryl sulfate, sodium cetyl sulfate, ammonium cocoyl isethionate, sodium lauroyl isethionate, and mixtures thereof.

11. A composition according to claim 10 wherein said anionic surfactant is sodium lauryl sulfate.

12. A composition according to claim 10 wherein said cationic surfactant is an ammonium salt having the formula:

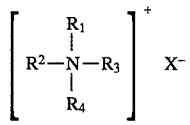

wherein in this formula for said ammonium salt, $R_1$ is an alkyl group having from about 12 to about 22 carbon atoms, $R_2$ is H or an alkyl group having from about 1 to about 22 carbon atoms, $R_3$ and $R_4$ are independently selected from H or an alkyl group having from about 1 to about 3 carbon atoms, and X is an anion selected form chloride, bromide, iodide, acetate, phosphate, nitrate, sulfate, methyl sulfate, ethyl sulfate, ethyl sulfate, tosylate, lactate, citrate, glycolate, and mixtures thereof.

13. A composition according to claim 10 wherein said cationic surfactant is selected from the group consisting of dilauryl dimethyl ammonium chloride, distearyl dimethyl ammonium chloride, dimyristyl dimethyl ammonium chloride, dipalmityl dimethyl ammonium chloride, and mixtures thereof.

14. A composition according to claim 12 wherein said composition further comprises from about 0.001% to about 20% of an active ingredient.

15. A composition according to claim 14 wherein said active ingredient is selected from the group consisting of selected from the group consisting of salicylic acid, benzoyl peroxide, cis-retinoic acid, trans-retinoic acid, retinol, phytic acid, N-acetyl L-cystein, azelaic acid, lipoic acid, resorcinol, lactic acid, glycol acid, ibuprofen, naproxen, hydrocortisone, phenoxyethanol, phenoxypropanol, phenoxyisopropanol, 2,4,4'-trichloro-2'-hydroxy diphenyl ether, 3,4,4'-trichlorocarbanilide, 2-ethylhexyl p-methoxycinnamic acid, oxybenzone, 2-phenylbenzimidazole-5-sulfonic acid, dihydroxyacetone, and mixtures thereof.

16. A composition according to claim 14 wherein said composition further comprises from about 0.1% to about 20% of a humectant.

17. A composition according to claim 16 wherein said humectant is glycerol.

18. A method for treating skin comprising the step of applying to the skin from about 0.5 mg/cm$^2$ to about 25 mg/cm$^2$ of the composition of claim 1.

19. A method for cleansing skin comprising the steps of
(i) applying to the skin from about 0.5 mg/cm$^2$ to about 25 mg/cm$^2$ of the composition of claim 1, and
(ii) rinsing the composition of claim 1 from the skin.

20. A method for cleansing skin comprising the steps of:
(i) applying to the skin from about 0.5 mg/cm$^2$ to about 25 mg/cm$^2$ of the composition of claim 1, and
(ii) wiping the composition of claim 1 from the skin.

21. A method of preparing a composition according to claim 1 comprising the steps of:
(i) combining an aqueous solution of said amphoteric surfactant and an aqueous solution of said anionic surfactant to form an aqueous dispersion of a complex of said amphoteric and said anionic surfactant, and
(ii) combining said aqueous dispersion of said complex with an aqueous solution of said cationic surfactant.

* * * * *

UNITED STATES PATENT AND TRADEMARK OFFICE
CERTIFICATE OF CORRECTION

PATENT NO. : 5,607,980
DATED : March 4, 1997
INVENTOR(S) : David Michael McAtee et al.

It is certified that error appears in the above-indentified patent and that said Letters Patent is hereby corrected as shown below:

In the Abstract, line 6 "conditioning desquamating" should read --conditioning, desquamating--.

At column 1, line 57 "have" should read --having--.

At column 1, line 58 "composition" should read --compositions--.

At column 2, line 9 "useful delivering" should read --useful for delivering--.

At column 2, line 12 "compositions, which" should read --compositions which--.

At column 2, line 19 after the second occurrence of "skin, for" insert --desquamating the skin, for--.

At column 4, line 2 "tendered" should read --rendered--.

At column 4, line 8 "rinse" should read --rinse-off--.

At column 4, line 13 "in the form" should read --in a form--.

At column 4, line 31 "composition" should read --compositions--.

At column 4, line 42 "drivatives" should read --derivatives--.

At column 4, line 46 "radical" should read --radicals--.

At column 4, line 48 "surfactant" should read --surfactants--.

At column 6, line 23 "where m" should read --wherein m--.

At column 6, line 40 "commercial" should read --commercially--.

At column 6, line 58 "the alkyl ether" should read --the alkyl and alkyl ether--.

At column 6, line 64 "alkoy isethonates" should read --alkoyl isethionates--.

At column 7, line 3 after "30" insert --carbon--.

At column 7, line 24 "cocyl" should read --cocoyl--.

UNITED STATES PATENT AND TRADEMARK OFFICE
CERTIFICATE OF CORRECTION

PATENT NO.     :     5,607,980

DATED          :     March 4, 1997

INVENTOR(S)    :     David Michael McAtee et al.

It is certified that error appears in the above-identified patent and that said Letters Patent is hereby corrected as shown below:

At column 9, line 6 "mixture" should read --mixtures--.

At column 9, line 16 "ammoniums" should read --ammonium--.

At column 9, line 17 "bromide tallow" should read --bromide, tallow--.

At column 9, line 58 "plasticers" should read --plasticizers--.

At column 10, line 6 "pathenol, pathenol" should read --panthenol, panthenol--.

At column 10, line 9 "material" should read --materials--.

At column 10, line 14 "compositions" should read --composition--.

At column 10, line 24 "ally" should read --allyl--.

At column 10, line 40 "or Orr" should read --to Orr--.

At column 10, line 48 "ingredients of" should read --ingredients or--.

At column 10, line 63 "a bout" should read --about--.

At column 11, line 17 "N-acetyl-L-cystein" should read --N-acetyl-L-cysteine--.

At column 11, lines 21-22 "phenoxisopropanol" should read --phenoxyisopropanol--.

At column 11, line 32 "N-acetyl-L-cystein" should read --N-acetyl-L-cysteine--.

At column 11, line 46 "microprofen" should read --miroprofen--.

At column 11, line 54 "hexyclaine" should read --hexylcaine--.

At column 12, line 7 "steaerate" should read --stearate--.

At column 12, line 9 "chlortetracycline," should read --chlortetracycline--.

At column 12, line 15 "mendelate" should read --mandelate--.

At column 12, line 19 "xyleneol" should read --xylenol--.

At column 12, line 21 "Sunscreen" should read --Sunscreening--.

At column 12, line 27 "Cosmetic" should read --Cosmetics--.

At column 12, lines 36-37 "4-isopropy" should read --4-isopropyl--.

UNITED STATES PATENT AND TRADEMARK OFFICE
CERTIFICATE OF CORRECTION

PATENT NO.    :   5,607,980

DATED         :   March 4, 1997

INVENTOR(S)   :   David Michael McAtee et al.

It is certified that error appears in the above-identified patent and that said Letters Patent is hereby corrected as shown below:

At column 13, line 7 "acid,2" should read --acid, 2--.

At column 13, line 13 "trichlorocarbailide" should read --trichlorocarbanilide--.

At column 13, line 21 "N-acetyl-L-cystein" should read --N-acetyl-L-cysteine--.

At column 13, line 22 "naproxen" should read --naproxen,--.

At column 13, line 29 "salicyclic" should read --salicylic--.

At column 14, line 25 "bout" should read --about--.

At column 14, line 29 "means" should read --mean--.

At column 14, line 36 "instance" should read --instances--.

At column 14, line 64 "cericite" should read --sericite--.

At column 14, line 66 "disoide" should read --dioxide--.

At column 15, line 2 "copolymers terpolymers" should read --copolymers, terpolymers--.

At column 15, line 3 "polyethlene" should read --polyethylene--.

At column 15, line 4 "polyethlene" should read --polyethylene--.

At column 15, line 33 "polyproylene" should read --polypropylene--.

At column 15, line 34 "Porpyltex" should read --Propyltex--.

At column 15, line 40 before "size" insert --particle--.

At column 15, line 42 "particles" should read --particle--.

At column 15, lines 48-49 after "polymethylstyrene," please insert --polypropylene, polystyrene, polyurethane, nylon, teflon, and mixtures thereof. Most preferred are--.

At column 15, line 61 "for noninoic" should read --are nonionic--.

At column 16, line 34 "glycolor" should read --glycol or--.

At column 16, line 61 "glycerl" should read --glyceryl--.

At column 16, line 63 "glycerl" should read --glyceryl--.

UNITED STATES PATENT AND TRADEMARK OFFICE
CERTIFICATE OF CORRECTION

PATENT NO.   :   5,607,980
DATED        :   March 4, 1997
INVENTOR(S)  :   David Michael McAtee et al.

It is certified that error appears in the above-identified patent and that said Letters Patent is hereby corrected as shown below:

At column 17, line 10 "polydroxyhydrocarbyl" should read --polyhydroxyhydrocarbyl--.

At column 17, line 19 "polydroxy" should read --polyhydroxy--.

At column 17, line 21 "10, 1960" should read --20, 1960--.

At column 18, line 9 "glucol" should read --glycol--.

At column 18, line 11 "glucol" should read --glycol--.

At column 18, line 12 "monesters" should read --monoesters--.

At column 18, line 54 "deglycerides" should read --diglycerides--.

At column 18, line 61 "drivatives" should read --derivatives--.

At column 19, line 6 "monesters" should read --monoesters--.

At column 19, line 18 "surcrose" should read --sucrose--.

At column 19, line 23 "carboyxlic" should read --carboxylic--.

At column 19, line 28 "behanate" should read --behenate--.

At column 19, line 31 "surcrose" should read --sucrose--.

At column 20, line 16 "Corning°" should read --Corning®--.

At column 20, line 22 "and Dow Corning" should read --Dow Corning--.

At column 20, line 25 "5), Dow" should read --5), and Dow--.

At column 20, line 45 "polymethyphenyl" should read --polymethylphenyl--.

At column 20, line 54 "caster" should read --castor--.

At column 20, line 55 "cottenseed" should read --cottonseed--.

At column 20, line 58 "caster" should read --castor--.

At column 20, line 59 "cottenseed" should read --cottonseed--.

At column 20, line 65 "polyproylene" should read --polypropylene--.

At column 21, line 10 "procedures" should read --procedure--.

UNITED STATES PATENT AND TRADEMARK OFFICE
CERTIFICATE OF CORRECTION

PATENT NO. : 5,607,980
DATED : March 4, 1997
INVENTOR(S) : David Michael McAtee et al.

It is certified that error appears in the above-indentified patent and that said Letters Patent is hereby corrected as shown below:

At column 21, line 14 "that is" should read --what is--.

At column 21, line 42 "along" should read --alone--.

At column 21, line 46 "produce" should read --product--.

At column 22, line 29 "peroxided" should read --peroxide--.

At column 23, line 65 "combined" should read --combining--.

At column 26, line 12 "Acucsrub" should read --Acuscrub--.

At column 26, line 59 "isethionate" should read --isethionates--.

At column 27, line 9 "from 11" should read --from about 11--.

At column 27, lines 17-18 "cocamidopropyl" should read --cocoamidopropyl--.

At column 27, line 42 "form" should read --from--.

At column 27, line 44 "ethyl sulfate, ethyl sulfate, tosylate" should read --ethyl sulfate, tosylate--.

At column 28, line 12 "N-acetyl-L-cystein" should read --N-acetyl-L-cysteine--.

At column 28, line 13 "glycol" should read --glycolic--.

Signed and Sealed this

Second Day of September, 1997

BRUCE LEHMAN

*Attest:*

*Attesting Officer*          *Commissioner of Patents and Trademarks*